(12) United States Patent
Fineberg

(10) Patent No.: US 6,508,801 B1
(45) Date of Patent: Jan. 21, 2003

(54) METHOD, COMPOSITION AND APPARATUS FOR RAPID AND ACCURATE PEDIATRIC RESUSCITATION AND EMERGENCY MEDICAL TREATMENT

(76) Inventor: S. Lee Fineberg, 47 Bound Station Rd., Stockton, NJ (US) 08559

( * ) Notice: Subject to any disclaimer, the term of this patent is extended or adjusted under 35 U.S.C. 154(b) by 0 days.

(21) Appl. No.: 09/384,615

(22) Filed: Aug. 27, 1999

Related U.S. Application Data

(60) Provisional application No. 60/098,140, filed on Aug. 27, 1998.

(51) Int. Cl.[7] ................................................ A61M 5/32
(52) U.S. Cl. ........................................ 604/416; 604/82
(58) Field of Search ................................ 604/24, 80–82, 604/416, 83–85, 87, 89; 128/897, 898

(56) References Cited

U.S. PATENT DOCUMENTS

| | | | | |
|---|---|---|---|---|
| 4,758,235 A | * | 7/1988 | Tu | 604/248 |
| 4,823,469 A | | 4/1989 | Broselow | 33/760 |
| 4,926,885 A | | 5/1990 | Hinkle | 128/898 |
| 5,292,535 A | * | 3/1994 | Kramer et al. | |
| 5,910,127 A | * | 6/1999 | Marangos et al. | |
| 6,132,416 A | * | 10/2000 | Broselow | 604/506 |

* cited by examiner

*Primary Examiner*—Manuel Mendez
(74) *Attorney, Agent, or Firm*—Lerner, David, Littenberg, Krumholz & Mentlik, LLP

(57) ABSTRACT

The present invention provides methods, compositions and apparati for rapid pediatric resuscitation and/or emergency management. A standardized formulation of each commonly used resuscitation medication is provided so that calculating dosage amounts is simplified. The formulations are standardized to a pre-determined dosage concentration and packaged in containers which may be coded to provide a simple means of separating and recognizing each medication. The standardized medications may be provided in a self-contained set-up along with commonly used medical equipment for use in resuscitation procedures.

18 Claims, No Drawings

METHOD, COMPOSITION AND APPARATUS FOR RAPID AND ACCURATE PEDIATRIC RESUSCITATION AND EMERGENCY MEDICAL TREATMENT

CROSS-REFERENCE TO RELATED APPLICATIONS

This application claims the benefit of U.S. Provisional application No. 60/098,140, filed Aug. 27, 1998, the disclosure of which is incorporated by reference herein.

FIELD OF INVENTION

This invention relates generally to methods and apparati for rapid pediatric resuscitation and/or emergency management of serious pediatric medical conditions.

BACKGROUND OF THE INVENTION

"Resuscitation" as used herein, generally refers to any form of pediatric advanced critical care or intervention necessitated by conditions including, but not limited to: cardiopulmonary arrest and/or arrhythmias, respiratory compromise, shock or shock-like states, intentional or unintentional drug or toxin ingestion/overdose, metabolic disorders, seizures, trauma and other potentially life threatening events. Each year there are thousands of pediatric resuscitations from these circumstances within the United States alone. However, despite such intervention, children still die. It is the hope of every care provider to decrease these statistics where possible.

One way to minimize loss of life sounds simple enough; minimize potential sources of error and eliminate sources of distraction. Anything that will allow the physician to concentrate more on a pediatric patient's condition and less on ancillary matters can improve the chance for a successful resuscitation. It is to this goal that the present invention is addressed.

Currently medical professionals have at their disposal approximately 20 different medications that are used during pediatric resuscitation and/or during the emergency management of pediatric medical conditions. These medications include, but are not limited to, epinephrine, atropine, lidocaine hydrochloride, etomidate, midazolam, ketamine, fentanyl citrate, morphine sulfate, thiopental sodium, succinylcholine chloride, pancuronium bromide, vecuronium bromide, lorazepam, diazepam, naloxone, adenosine, calcium gluconate, dextrose, sodium bicarbonate, phenyltoin, phenobarbital sodium, fosphenyltoin, mannitol and other medications indicated for similar therapeutic uses. These medications have been extensively researched and are currently indicated or recommended as part of the advanced pediatric resuscitation protocols as outlined by the American Academy of Pediatrics and the American Academy of Emergency Physicians.

However, in contrast to the relatively standard, regimented and documented dosing of such medications to adult patients during a resuscitation attempt, the dosages for pediatric patients can vary widely. This can be attributed to the relative difference in lean body mass within the pediatric population as a whole. Since the body weight of most adults is in excess of what is deemed necessary to calculate the maximum recommended dose of a given medication, standard dosages are generally the rule and not the exception during adult resuscitation. On the other hand, significant variation in the lean body mass of pediatric patients can exist below the "standard dosage" typically administered to adult patients (i.e., given similar medical conditions, a premature infant would generally not receive the same dose of medication as a fully matured adolescent). If a patient is below that weight which results in the "standard dosage" (as is the case with most pediatric patients) then, the respective requirements for pharmacotheraphy during resuscitation will be determined by factors such as that patient's weight. The variation in weight, along with corresponding variation in dosage, combined with the nature of pediatric resuscitation in general, has been shown to result in a significant number of errors in medication administration. In fact, one study indicated that both out-of-hospital and in-hospital care providers inaccurately dose medications during pediatric resuscitation in 64% and 83% of the time, respectively, with dosing errors ranging from 2% to 769% of the correct amount.

At this time, there are several methods employed by pediatric and emergency specialists to assist with pediatric resuscitation. Traditional approaches include rote memorization of the required medications and appropriate dosages (which carries with it the highest potential for egregious error), memory adjuncts such as reference cards and tables, or the relatively new Broselow Pediatric Emergency Tape (which lists standard resuscitation medications and their dosages on a tape with weight corresponding to length/height as measured during the course of resuscitation). This device is disclosed in, for example U.S. Pat. Nos. 4,823,469 and 4,713,888.

While the foregoing methods are effective if utilized appropriately, they have significant limitations. For instance, a medical professional may be required to perform serial conversions from weight in milligrams to a corresponding solution volume in milliliters depending on the number of medications required. In addition, each medication may vary in quantity, concentration and subsequent volume of the medication administered. This is primarily due to the fact that most resuscitation medications are manufactured in different concentrations and dosage forms, and thereby lack dosage and/or concentration uniformity. As a consequence of these dosage variations and the emergent nature of the situation, insufficient time for a detailed system of "checks" during dose computation, information and/or drug acquisition and subsequent administration, a patient may receive either an insufficient or an excessive quantity of an appropriate medication. When one is dealing with infants and small children, a simple error or an incorrect placement of a single decimal point may mean the difference between regaining life or losing a life entirely.

Accordingly, there is a need in the art for methods and tools which give the care providers and their patients the optimal chance for a successful outcome.

The present invention fulfills these and other needs by providing rapid, uniform and systematic method of, and apparatus for, administering pediatric resuscitation medications.

SUMMARY OF THE INVENTION

In accordance with the present invention, a standardized pediatric resuscitation formulation is provided. The formulation includes an active agent useful in pediatric resuscitation which is provided in a predetermined amount. A pharmaceutically acceptable carrier and, optionally, a diluent or other excipient, can be provided as well. This carrier or carrier and diluent are provided in an amount which is sufficient to result in a predetermined concentration of the active agent. The concentration of this active agent is selected such that a standardized dose when multiplied by the patient's "unit", such as weight, will deliver an amount of the active agent which is appropriate for pediatric resuscitation. If two particular active agents are provided as part of a system of standardized doses, for example, the concentrations of drug in each may be widely different. That is, the amount of active agent per unit of carrier may vary significantly from one medication to the other. Similarly, the appropriate amount of each active agent to be administered to a patient to accomplish pediatric resuscitation may vary widely. Perhaps several milligrams of a first drug are administered where only a few tenths of a milligram of a second drug are needed. However, the volume of the formulation of each, administered for pediatric resuscitation, would be identical when standardized in accordance with the present invention. Thus, in each case, a patient who is 10 kg by weight might receive 1 ml of each of the drug formulations for the appropriate medical condition. Again, however, the concentration of each drug in those doses and the absolute amount of active agent administered in each case may be significantly different from one drug to the other. Methods of administering these standardized formulations and kits or other set-ups containing the standardized formulations are also contemplated.

The present invention will allow for the care provider to quickly determine the correct medication dosage for a pediatric patient without the need to reference complicated dosage charts or recall mathematical formulation conversions.

The present invention permits accurate and relatively error-proof dosage determinations by providing standardized dosages for commonly used resuscitation medications. According to the present invention, commonly used resuscitation medications are formulated to conform to a pre-set dosage standard. Any standard may be used. For example a standard may be arbitrarily set by, for example, a medical association concerned with the practices and procedures of pediatric treatment. Alternatively, the standard may be based on a study that suggests an optimum dosage concentration amenable to the physical and pharmacokinetic properties of the resuscitation medications. In either case, the standard used to formulate the medications will dictate their concentrations and dosages. An example of such a standard according to the invention could be based on a power of five or ten, (i.e., 0.05 or 0.1 cc/kg) or according to any other convenient numerical whole number or integer system. According to the present invention, a treating care provider would only need to calculate the dosage amount once and use that calculated amount for the administration of similarly standardized medications.

Another aspect of the present invention provides a method of calculating dosage amounts and administering medication to a pediatric patient based on that patient's actual or estimated weight and using a modified system with specially adjusted concentrations of medications. Actual or estimated weight determinations may be accomplished through known methods such as physically weighing the patient with a scale. A modified scale could also give a means to provide the practitioner with a list of additional material that might be required during the emergency medical treatment of that patient that corresponds to the patient's weight (i.e., a printout, a list on the side of the scale, etc.). A patient's weight might also be estimated, for example, through the use of a measuring tape (or disposable paper outline) which correlates the length (or circumference) of the patient to an average mean weight based on the 50th percentile from weight/height relationships commonly used in standard pediatric growth charts. In addition a tape could provide a means to incorporate algorithms correlating the child's estimated weight with suggested dosages.

It is another aspect of the invention to provide a method and apparatus whereby assisting or supervising care providers can verify the primary care provider's calculations very quickly at a glance without the need of computing or converting unit measures. This is possible because all of the medications are dosed according to the same adjusted/standardized concentrations and all of the administered dose would therefore correspond to one calculation.

It is another aspect of the present invention to provide a medical set-up containing all anticipated resuscitation drugs in either standardized aliquots or multi-use dose vials and optionally, a height/weight/dosage measuring tape (or similar device for the patient weight determination/estimation), and any commonly used resuscitation devices. The above-described set-ups may be stocked in hospitals, clinics, fire and police stations, or anywhere it is anticipated that pediatric resuscitation may be performed. The set-ups may be manufactured so that they are completely disposable, or optionally, the kits may be re-stocked after each use.

It is another aspect of the invention to provide a cost effective pediatric resuscitation method and apparatus whereby little or no medication is wasted. This is because the system could allow for the specially adjusted concentrations of medication to be offered in "multi-use" vials. This system would not necessarily require that medication be packaged in individual pre-measured aliquots and could therefore reduce production costs.

It is yet another aspect of the invention to provide individual single-use ampoules or other containers for use in situations where multi-use bottles are not practical.

It is still another aspect of the invention to provide the standardized medications in bottles with specific indicia relative to each medication's sequential use, category, grouping or tier in a resuscitation procedure. For example, the medications may be grouped into tiers corresponding to therapeutic class or order of anticipated administration. Each bottled medication belonging to a tier may be commonly color-coded or shaped differently from another tier. Alternatively, the tiers may consist of bottles having a specific texture or unique label that is readily identifiable.

DETAILED DESCRIPTION OF THE INVENTION

The methods and apparatus of the present invention are based on the concept that the drugs also referred to as medications or active agents, and medical devices used for pediatric resuscitation should be as easy to use as possible thus allowing the care provider to devote the maximum amount of life-saving attention to the patient while minimizing the chance of error. The present invention provides methods, compositions and apparatus that greatly facilitates rapid resuscitation treatment of the pediatric patient.

One feature of the present invention provides for the standardization of resuscitation medications. By standardizing the volume per unit also known herein as a "standardized dose," of each drug in solution to a common level or factor, the care provider can quickly determine the amount of each formulation to be administered.

In order to fully appreciate the present invention, it is first necessary to describe the conventional methods of administering pediatric resuscitation medications. Conventionally, resuscitation medications are available in a preselected concentration by the drug manufacturer. The concentration and therefore the amount of a formulation of a particular drug to be administered per unit (size, weight or surface, etc.) are of the patient will be independent compared to any other resuscitation medication. See Table 1. While not intended to be exhaustive, Table 1 lists several commonly used resuscitation medications along with their concentrations and dosages in solution as currently available.

TABLE 1

| # | Drug | Pharm Co | Current Dosage | Current Concentration | Modified ($E = S^2$) Dosage | Modified ($E = S^2$) Concentration | Notes |
|---|------|----------|----------------|----------------------|-----------------------------|-------------------------------------|-------|
| Tier 1 Resuscitation Drugs | | | | | | | |
| 1 | Epinephrine (1:1000) | Astra, Elkin-Sinn | 0.1 ml/kg | 1 mg/kg | 0.1 cc/kg | 1 mc/kg | p. 552; High Dose Epi. |
|   | Epinephrine (1:10000) | Astra, Elkin-Sinn | 0.1 ml/kg | 0.1 mg/ml | 0.1 cc/kg | 0.1 mg/cc | Low Dose Epi. |
| 2 | Atropine | Astra | 0.02 mg/kg | 0.1 mg/kg | 0.1 cc/kg | 0.2 mg/cc | p. 541 PDR; water soluble; min. dose 0.5 cc, max. dose 5 cc |
|   |  | Ohmeda | 0.02 mg/kg | 0.4 mg or 1 mg/ml | 0.1 cc/kg | 0.2 mg/cc | p. 1932 PDR; water soluble; min. dose 0.5 cc, max. dose 5 cc |
| 3 | Lidocaine hydrochloride | Astra | 1–2 mg/kg | 10 mg or 20 mg/ml | 0.1 cc/kg | 20 mg/cc | p. 585 PDR |
| Tier 1 Induction Agents/Sedatives | | | | | | | |
| 4 | Etomidate | Abbotts, Am Regent | 0.2 mg–0.3 mg/kg | 2 mg/ml | 0.1 cc/kg | 2 mg/cc | Mod dose is low end of rec range. If conc to 3 mg/cc then 0.1 cc/kg would represent high end of rec dose range |
| 5 | Midazolam (Versed ™) | Roche | 0.1 mg–0.2 mg/kg | 1 mg or 5 mg/ml | 0.1 cc/kg | 1 mg/cc | p. 2512 PDR; patented; water-sol as HCl |
| 6 | Ketamine | Bedford | 1–2 mg/kg | 50 mg/ml | 0.1 cc/kg | 20 mg/cc | Not in PDR; water soluble; 0.1 cc/kg yields 2 mg/kg at this conc. |
| 7 | Fentanyl Citrate | Astra, Elkin-Sinn | 1–5 mg/kg | 0.05 mg/ml | 0.1 cc/kg | 0.5 mg/cc | p. 554 PDR; 0.1 cc/kg yields 5 mcg/kg at this conc. |
| 8 | Morphine Sulfate | Astra, Elkin-Sinn | 0.1 mg-0.2 mg/kg | 0.5 mg, 1 mg or 25 mg/ml | 0.1 cc/kg | 1 mg/cc | p. 539 & 561 PDR; 0.1 cc/kg yields 0.1 mg/kg |
| 9 | Thiopental Sodium | Ohmeda | 3 mg–5 mg/kg | 25 mg/ml | 0.1 cc/kg | 30 mg–50 mg/cc | p. 1941 PDR; potency of 0.1 cc/kg dose depends on conc able to achieve |
| Tier 1 Paralytics | | | | | | | |
| 10 | Succinulcholine Chloride | Glaxo-Wellcome, Organon | 1 mg–2 mg/kg | 20 mg/ml | 0.1 cc/kg | 20 mg/cc | p. 1003 and 1959 PDR; water soluble |
| 11 | Pancuronium Bromide | Astra, Elkin-Sinn, Ohmeda, Organon | 0.01 or 0.1 mg/kg | 1 mg or 2 mg/ml | 0.1 cc/kg | 0.1 mg or 1 mgcc | p. 568 & 1955 PDR; water soluble |
| 12 | Vecuronium Bromide | Organon | 0.01 or 0.1 mg/kg | 1 mg/ml | 0.1 cc/kg | 0.1 mg or 1 mgcc | p. 1951 PDR |
| Tier 1 Seizure Drugs | | | | | | | |
| 13 | Lorazepam | Wyeth-Ayerst | 0.05 or 0.1 mg/kg | 2 mg or 4 mg/ml | 0.1 cc/kg | 1 mgcc | P. 3011 PDR; soluble in NaCl |
| 14 | Diazepam | Roche, Elkin-Sinn, Ohmeda | 0.2 or .4 mg/kg | 5 mg/ml | 0.1 cc/kg | 3 mg or 4 mgcc | p. 898 & 2525 PDR |

TABLE 1-continued

| # | Drug | Pharm Co | Current Dosage | Current Concentration | Modified (E = S²) Dosage | Modified (E = S²) Concentration | Notes |
|---|------|----------|----------------|----------------------|--------------------------|----------------------------------|-------|
| Tier 1 Others | | | | | | | |
| 15 | Naloxone | Astra, Elkin-Sinn | 0.1 mg/kg | 0.4 mg or 1 mg/ml | 0.1 cc/kg | 0.4 mg/cc | p. 561 PDR |
| 16 | Adenosine | Fujisawa | 0. mg–0.25 mg/kg | 3 mg/ml | 0.1 cc/kg | 1.25 mg/cc | May double dose on second attempt to chemically cardiovert |
| Tier 2 Resuscitation Drugs | | | | | | | |
| 17 | Calcium gluconate | | 1 ml/kg | | 1 cc/kg | | |
| 18 | Dextrose 50% injection | Astra | 2–4 ml/kg as D25 | 500 mg/ml | 2–4 cc/kg | 250 mg/cc | If 1 cc/kg then repeat doses indicated |
| 19 | Sodium bicarbonate | Astra | 1 ml/kg | 1 meq/kg child; 0.5 meq/kg infant | 1 cc/kg | 1 meq/cc | p. 577 PDR |
| Tier 2 Seizure Drugs | | | | | | | |
| 20 | Phenytoin | Elkin-Sinn | 15 mg–20 mg/kg | 50 mg/ml | 1 cc/kg | 20 mg/cc | p. 899 PDR; compatible w/NaCl; rate listed on spool |
| 21 | Phenobarbitol Sodium | | 10 mg–20 mg/kg | 65 mg or 130 mg/ml | 1 cc/kg | 20 mg/ml | Rate not to exceed 2.5 cc/minute |
| 22 | Fosphenytoin ™ | Parke-Davis | 15–20 mg PE/kg (PE = phenytoin equivalents) | 75 mg/ml–50 mg/ml phenytoin | 1 cc/kg | 20 mg/cc | p. 2077 PDR; this conc. refers to dose at administration (diluted w/DSW) |
| Tier 2 Other | | | | | | | |
| 23 | Mannitol | | 0.25–0.5 g/kg | 1 g/5 ml | 1 cc/kg | 1 g/4 cc | May repeat to max. dose 4 cc/kg over 4–6 hours |

Atropine, for example, has a suggested dosage of 0.02 mg/kg and is provided by the manufacturer in a concentration of 0.1 mg/ml. In order for a care provider to give the proper dosage to a child weighing 10 kg, a calculation must be made to determine exactly what volume of the medication is to be administered. For Atropine, a proper dosage would beg calculated as such:

Dosage=10 kg (patient weight)×0.02 mg/kg (suggested dosage)= 0.2 mg Atropine.

Medication Volume to be administered=0.2 mg/0.1 mg/ml=2 ml Atropine solution.

Because each drug listed in Table 1 has its own dosage and concentration, the above calculation must be performed for almost every medication administered. The opportunity for error is significant due to these conversions and mathematical calculations which need to be performed rapidly and under the very tense, noisy and crowded condition of an emergency room. Errors and wasted time could easily result in a fatality during the resuscitation procedure.

By contrast, if resuscitation medications were formulated to a single uniform standardized dose or dosage, for example 0.1 cc/kg, then a care provider would only need to perform a single, easy dose calculation.

The present invention provides for a much simpler method of calculating the dosage of resuscitation medications by using, in part, a "standardized dose" for medications used in pediatric resuscitation procedures. "Standardized" dose means a uniform volume of the formulation containing the active agent which can be drawn and administered on a per "unit" basis. Thus for 2 standardized formulations, the administered dose for each will be the same volume even though the amount and concentration of the active agent will be different. "Unit" means any measure of a patient used for calculating dosing. These may include weight, length, surface area, and the like. For convenience and ease of understanding, weight will be used to describe the invention. However, any unit may be used.

A standardized dose can be, for example, a uniform volume of the formulation containing the active agent which can be drawn and administered to a patient on a per kilogram basis. "Standardized dose" should not be confused with "standardized administered dose" which is the result of the dose computation. By way of example, if a patient is 10 kg and the standardized dose is 1 cc/kg, the standardized administered dose is 10 cc. This is the volume of the drug containing formulation which will actually be administered to the patient.

When a care provider determines, for example, the weight of a patient, a simple calculation would determine the volume of formulation to administer. Using such a standard, calculating the standardized administered dosage of any of the standardized medications is made simple because it is merely a matter of multiplying the standardized dose by the patient's weight. Because the concentrations of each medication are different, the amount of each drug which will be administered will vary widely, from formulation to formulation. However, the volume or amount of each formulation which will be measured out and administered will be the same for each patient of identical weight.

Furthermore, because the patient's weight is a constant parameter for that patient, each resuscitation medication set to the same standard required by that patient would be administered in exactly the same volume. No further calculations are necessary.

According to the present invention, the standard may be promulgated, by for example, a medical association concerned with the treatment of pediatric patients or a consortium of care providers responsible for emergency treatment, or any other organization studying improved treatment of pediatric resuscitation patients. The standard may be arbitrary of based on a study, for example, suggesting the optimum standardized concentration that is suitable for the specific medications used in resuscitation. As provided by the invention, such standardized formulations could be produced by the drug manufacturers or optionally reformulated and packaged by a third party.

In order to practice the invention, a drug manufacturer, for example, would provide a formulated medication, and would adjust the concentration in which the drug is diluted to conform to a pre-determined standard. The formulated medication would include one or more active agents useful for, amongst other things, pediatric resuscitation (including their physiologically acceptable salts, esters and the like) pharmaceutically acceptable carriers, and where appropriate, diluents or solvents such as water or alcohol. Other ingredients may include adjuvants, surfactants, stabilizers, co-solvents and buffers. Of course, if present, these ingredients must be factored into the concentration.

Many of the commonly used medications in reformulated form are provided in Table 1. Once again using Atropine as an example in Table 1, assuming that doses are standardized according to the present invention to, for example a standardized dose of 0.1 ml/kg (or 0.1 cc/kg), then the concentration of the drug must be adjusted to 0.2 mg/ml. These modifications made according to the present invention would allow for the patient to receive the same amount of active agent as conventionally administered and appropriate for pediatric resuscitation, the difference being that the care provider administering the active agent would have a simpler and quicker method of calculating the volume of each formulation to be administered.

It is another aspect of the present invention to divide commonly used resuscitation medications into groups or Tiers. Each Tier may correspond to the sequential order of use in a typical resuscitation procedure, or the indicated therapeutic class of treatment, or any other suitable categorization scheme that organizes the medications for easy reference and availability. Different Tiers may be standardized to yield different standardized doses. Preferably, members of each individual Tier have the same standardized dose. So Tier 1 may provide standardized doses of 0.1 cc/kg while all of the medications in Tier 2 provide standardized doses of 1.0 cc/kg.

In one example where the Tiers are organized by sequential order of administration, Tier 1 drugs would be considered first line medications, which are generally administered immediately to the patient. Such Tier 1 drugs, in accordance with the present invention, may be color-coded, placed in different shaped bottles, labeled, etc., so one can quickly determine that the bottle contains a standardized formulation, that it is a member of a specific Tier and/or that the formulation within has a specific standardized dose. The care provider may then rapidly select all first line, Tier 1 drugs and administer them using a single volume as calculated according to the above described example. Color-coding or using another form of rapid identification may reduce the amount of time spent locating the appropriate medications.

Once the care provider has administered the Tier 1 medications, he can proceed to Tier 2 which is separated from Tier 1 and may have the same or different standardized dosing as Tier 1, but in any case would be easily calculated. The standardized resuscitation medication in the Tier would be bottled, or labeled in a manner which is easily recognizably different than Tier 1. Administration of Tier 3 would follow a similar system as Tiers 1 and 2.

As noted above, any method of quickly identifying and discriminating standardized doses, such as, without limitation, color-coded bottles or containers, color-coded labels or caps, different shaped bottles or containers, textured finishes on the bottles of containers, or other indicating features capable of designating to which Tier a particular bottle or container belongs or what dosage factor is contained therein is contemplated. The standardized medications may be distributed in, for example 1 ml ampoules for ease of use and to reduce the waste associated with opening a large bottle of medication and discarding most of the contents because only a small percentage was consumed. Alternatively, the medication may be dispensed in multi-use vials, whereby, a larger, multi-dose bottle is re-stocked for another use.

It is yet another aspect of the invention to provide a medical set-up containing a plurality of Tiered drug bottles or containers which have been formulated to correspond to pre-determined standardized dosage as described above together with a retractable weight/height measuring tape as well as any medical devices commonly used in pediatric resuscitation procedures. The set-up may be in the form of a kit, according to the present invention, and may be housed on a convenient carrying case or suitable for mounting to a wall, operating table, hospital bed or other location likely to be used for performing resuscitation procedures. Alternatively, the set-up may be contained in a cabinet or drawer located close to where resuscitation procedures are performed.

In a preferred embodiment of the present invention, the resuscitation medications commonly used in pediatric resuscitation procedures are standardized to a dosage of between about 0.001 and 3.0 cc/unit. More preferably, the dosage is standardized between about 0.001 and 1.0 cc per unit, and more preferably, to a standardized dose of 0.01 cc per unit.

In a preferred embodiment of the present invention, the resuscitation medications commonly used in pediatric resuscitation procedures are standardized by the drug manufacturers to a dosage based on a power of ten. More preferably the dosage is standardized to 0.1 cc/kg.

In another preferred embodiment of the method of administering resuscitation medications, the care provider measures the pediatric patient with a retractable measuring tape, then estimates the weight of the patient based on the correlation weight/height data provided on the tape or posted charts located in the area of the procedure. In another aspect of the invention, the child's weight is estimated using a retractable tape measure which correlates the length of the patient with an approximate weight based on the 50th percentile of weight/height relationships taken from standard pediatric charts. Similarly, an estimation of patient weight may be obtained by other mechanical means or by direct measurement such as a scale or trace-out imprinted on a patient table corresponding to estimated weights based on length. While the discussions herein are directed to weight, it should be understood that by the term weight, it is intended to include size, surface area or any other number which can be generalized and multiplied by the dosage factor to determine the volume of standardized resuscitation medication to administer. The care provider then calculates the volume of standardized administrative dose of the medication to administer to the patient.

In another preferred embodiment, a set-up is assembled to include a housing made of a resilient or flexible material such as a plastic case or cloth bag. In the container is a set of all commonly used resuscitation medications standardized to 0.1 ml/kg and color-coded to correspond to each Tier. The set-up may also contain other medical devices commonly used in resuscitation. Each set-up may optionally contain a list of recommended equipment sizes or device settings based on patient weight such as: bag-valve-masks, endotracheal tubes and laryngoscope blades, oral and nasotracheal airways, ventilator settings, doses of common antibiotics, antidotes and dosages to common toxic ingestions, etc.

The invention is further described with reference to the following examples:

EXAMPLE 1

A child is brought to a physician in extremis. He is rapidly approaching respiratory failure. The physician determines the weight of the child to be approximately 10 kg by using a measuring tape that correlates height with weight of average children. According to the invention, if the child weighs 10 kg, a dose of 1 cc of each resuscitation medication would be the appropriate quantity to administer to this child if all of the medications have been formulated to a standardized concentration. Each medication would be administered in a 1 cc dose and no further calculation would be necessary.

EXAMPLE 2

A three year old boy is brought in by the paramedics to the local ER. The physician opens a resuscitation set-up which has been assembled according to the present invention. The physician measures the child's length and extrapolates the child's weight based on correlation tables included on charts located in the set-up. The patient's estimated weight is approximately 16 kg. Based on child's estimated weight, the physician decides to administer 1.6 cc of Tier 1 medications which are supplied in the set-up and color-coded blue. All the medications have been provided in standardized dosage form according to the present invention. As the physician notes the child's condition through the course of treatment, he realizes that it will be necessary to administer Tier 2 medications which are also located in the set-up and are color-coded red. Similarly, Tier 3 drugs which are color-coded green, are administered as necessary.

Table 1 lists the current dosages and concentrations for some of the medications used commonly during resuscitation as well as the modified dosage and concentration of the invention. This table is meant to illustrate an example of how these drugs might be reformulated so as to yield a common denominator with respect to dosing (i.e., 0.1 cc/kg). It should not be construed to represent the only possibility but should serve to merely illustrate the method/theory by which such a system might be created and employed in practice. While specific embodiments have been shown and described, many variations exist.

In addition, as new medications are constantly being researched, developed and added to our armamentarium of drugs used for the purpose for resuscitation, Table 1 should not be considered to contain those medications that have yet to be developed or approved for resuscitation. However, should such medications be developed and approved for use in accordance with PALS/ACLS protocols/algorithms, the common dosage denominator of the invention could then be applied to them as well.

Having described the invention in detail, those skilled in the art will appreciate that modifications may be made of the invention without departing from its spirit. Therefore, it is not intended that the scope of the invention be limited to the specific embodiments illustrated and described.

I claim:

1. A standardized pediatric resuscitation formulation comprising:

(a) an active agent useful in pediatric resuscitation provided in a predetermined amount; and (b) a pharmaceutically acceptable carrier provided in an amount which is sufficient to provide a predetermined concentration of said active agent such that a standardized dose of said formulation delivers a standardized administered dose including an amount of said active agent which is appropriate for pediatric resuscitation.

2. The formulation according to claim 1 further comprising a diluent wherein said active agent, said pharmaceutically acceptable carrier and said diluent are provided in amounts which are sufficient to result in a predetermined concentration of said active agent such that a standardized dose thereof will deliver a standardized administered dose including an amount of said active agent which is appropriate for pediatric resuscitation.

3. The formulation according to claim 1 wherein said predetermined standardized dose is between 0.001 and 3.0 cc/unit.

4. The formulation according to claim 3 wherein said predetermined standardized dose is between 0.01 and 1.0 cc/unit.

5. The formulation according to claim 4 wherein said predetermined standardized dose is 0.1 cc/unit.

6. The formulation according to claim 1 supplied in a container which indicates that it contains a standardized pediatric resuscitation formulation, that the standardized pediatric resuscitation formulation contained therein contains a standardized dose or both.

7. The formulation according to claim 6 wherein said container is shaped so as to indicate a standardized pediatric resuscitation formulation, that the standardized pediatric resuscitation formulation contained therein contains a standardized dose or both.

8. The formulation according to claim 6 wherein the container is color-coded so as to indicate a standardized pediatric resuscitation formulation, that the standardized pediatric resuscitation formulation contained therein contains a standardized dose or both.

9. The formulation according to claim 6 wherein the container is textured so as to indicate a standardized pediatric resuscitation formulation, that the standardized pediatric resuscitation formulation contained therein contains a standardized dose or both.

10. The formulation according to claim 6 wherein the container includes printed indicia so as to indicate a standardized pediatric resuscitation formulation, that the standardized pediatric resuscitation formulation contained therein contains a standardized dose or both.

11. A method of administering resuscitation medications to a pediatric patient comprising the steps of:

(a) estimating a unit of the patient;

(b) measuring a standardized administered dose of resuscitation medication based upon said unit and a standardized dose of said resuscitation medication; and (c) administering said administered dose of said resuscitation medication formulated to said patient.

12. The method according to claim 11 further comprising the step of selecting a resuscitation medication formulation from among a plurality of resuscitation medication formulations which have each been standardized to provide same standardized dose.

13. The method according to claim 12 wherein said standardized dose is between 0.001 and 3.0 cc/unit.

14. The method according to claim 12 wherein said standardized dose is between 0.01 and 1.0 cc/unit.

15. The method according to claim 12 wherein said standardized dose is 0.1 cc/unit.

16. The method according to claim 12 wherein said resuscitation medication is supplied in a container which indicates that it contains a standardized pediatric resuscitation formulation, that said standardized pediatric resuscitation formulation contained therein contains a standardized dose or both.

17. The method according to claim 16 wherein said container is color-coded so as to indicate a standardized pediatric resuscitation formulation, that the standardized pediatric resuscitation formulation contained therein contains a standardized dose or both.

18. The method according to claim 16 wherein said container includes printed indicia so as to indicate a standardized pediatric resuscitation formulation, that the standardized pediatric resuscitation formulation contained therein contains a standardized dose or both.

* * * * *